United States Patent
Ashmore

(10) Patent No.: US 12,097,298 B1
(45) Date of Patent: Sep. 24, 2024

(54) STERILIZING CURRENCY COUNTER

(71) Applicant: Carla Ashmore, Dallas, TX (US)

(72) Inventor: Carla Ashmore, Dallas, TX (US)

( * ) Notice: Subject to any disclaimer, the term of this patent is extended or adjusted under 35 U.S.C. 154(b) by 424 days.

(21) Appl. No.: 17/504,181

(22) Filed: Oct. 18, 2021

Related U.S. Application Data

(60) Provisional application No. 63/092,620, filed on Oct. 16, 2020.

(51) Int. Cl.
*A61L 2/26* (2006.01)
*A61L 2/10* (2006.01)
*A61L 2/18* (2006.01)
*G06M 7/06* (2006.01)

(52) U.S. Cl.
CPC ........ *A61L 2/26* (2013.01); *A61L 2/10* (2013.01); *A61L 2/18* (2013.01); *G06M 7/06* (2013.01); *A61L 2202/11* (2013.01)

(58) Field of Classification Search
CPC ..... A61L 2/26; A61L 2/10; A61L 2/18; A61L 2202/11; G06M 7/06
See application file for complete search history.

(56) References Cited

U.S. PATENT DOCUMENTS

| | | | |
|---|---|---|---|
| 5,374,814 | A | 12/1994 | Kako et al. |
| 9,415,124 | B2 | 8/2016 | Baek |
| D855,103 | S | 7/2019 | van Slooten |
| 10,850,184 | B1 | 12/2020 | Colvin |
| 2011/0253563 | A1 | 10/2011 | Goldman |
| 2015/0359914 | A1* | 12/2015 | Baek .......... A61L 2/14 250/455.11 |
| 2017/0021043 | A1 | 1/2017 | Baek |
| 2021/0260231 | A1* | 8/2021 | Andrews ........... A61L 2/10 |

FOREIGN PATENT DOCUMENTS

CN 2629705 Y 4/2004
WO WO 2015/194713 12/2015

* cited by examiner

*Primary Examiner* — Nicole M Ippolito
(74) *Attorney, Agent, or Firm* — Kenneth L. Tolar

(57) ABSTRACT

A currency sterilizing machine includes an internal sorting, counting, and stacking mechanism of the type found in conventional currency-counting devices. Within the housing interior is a sterilizing device for disinfecting currency as it passes through the machine. The sterilizing device is either a spray nozzle for dispensing a disinfectant or a plurality of UVC radiators for destroying microorganisms.

7 Claims, 6 Drawing Sheets

STERILIZING CURRENCY COUNTER

CROSS REFERENCE TO RELATED APPLICATIONS

This application claims priority of provisional application No. 63/092,620 filed on Oct. 16, 2020, the specification of which is incorporated herein by reference.

BACKGROUND OF THE INVENTION

The present invention relates to a machine that sterilizes currency as it is being counted.

DESCRIPTION OF THE PRIOR ART

Paper currency is constructed from pulp formed of cotton, linen, and other various components. The resulting paper is highly porous and therefore easily harbors dangerous microbes, such as bacteria and viruses. Several studies have confirmed the existence of significant amounts of bacteria on paper currency. Though coins are not as porous, their exterior surfaces are also coated with numerous organisms. Because many businesses, particularly banks, process a large amount of currency through counting machines, incorporating a sterilizing mechanism would efficiently decontaminate currency.

Accordingly, there is currently a need for a device that removes harmful organism from currency. The present invention addresses this need by providing a counting machine that disinfects currency as it is being counted.

SUMMARY OF THE INVENTION

The present invention relates to a currency sterilizing machine including an internal sorting, counting, and stacking mechanism of the type found in conventional currency-counting devices. Within the housing interior is a sterilizing device for disinfecting currency as it passes through the machine. The sterilizing device is either a spray nozzle for dispensing a disinfectant or a plurality of UVC radiators for destroying microorganisms.

It is therefore an object of the present invention to provide a disinfecting currency-counting machine.

It is therefore another object of the present invention to provide a disinfecting currency-counting machine that projects UV radiation onto currency being counted.

It is yet another object of the present invention to provide a disinfecting currency-counting machine that minimizes disease transmission associated with handling money.

Other objects, features, and advantages of the present invention will become readily apparent from the following detailed description of the preferred embodiment when considered with the attached drawings and the appended claims.

DESCRIPTION OF THE PREFERRED EMBODIMENT

Figure 1:
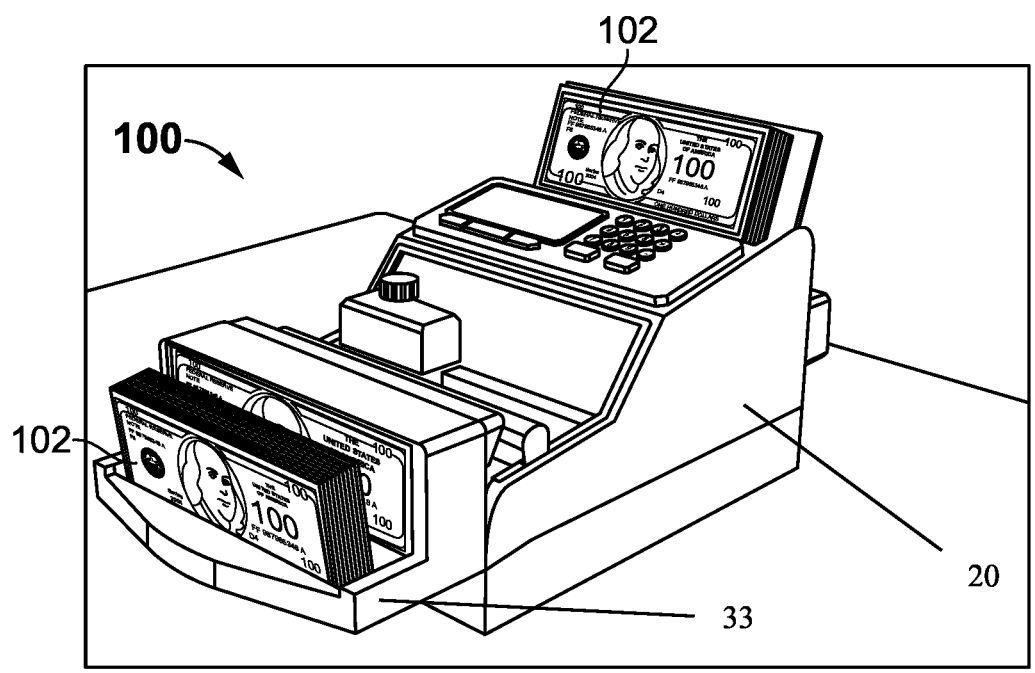
FIG. 1 is a perspective view of the currency-counting machine according to the present invention.

The present invention relates to a sterilizing currency-counting machine 100 for sorting, counting and sterilizing paper currency or bank notes 102. The machine comprises a housing 20 having a bottom surface, a top surface, a plurality of sidewalls, a front end, a rear end, and an interior chamber. Within the interior chamber is a sorting and counting mechanism of the type typically found in existing counting machines. The sorting mechanism includes a software application and a plurality of stacking rollers 122 for sorting and stacking counted currency in a conventional fashion. The top surface of the housing includes a hopper 118 having a sensor that informs the machine electronics that notes are present. Adjacent the hopper is a keypad 112 for selecting a desired output, such as total count or note value, which is depicted on a display 114. The keypad includes a button 116 for activating a UVC sterilizing means described below. The front end of the housing includes a stacking tray 33 for receiving counted currency; the tray 33 includes a sensor 124 for detecting bank notes.

Figure 2:
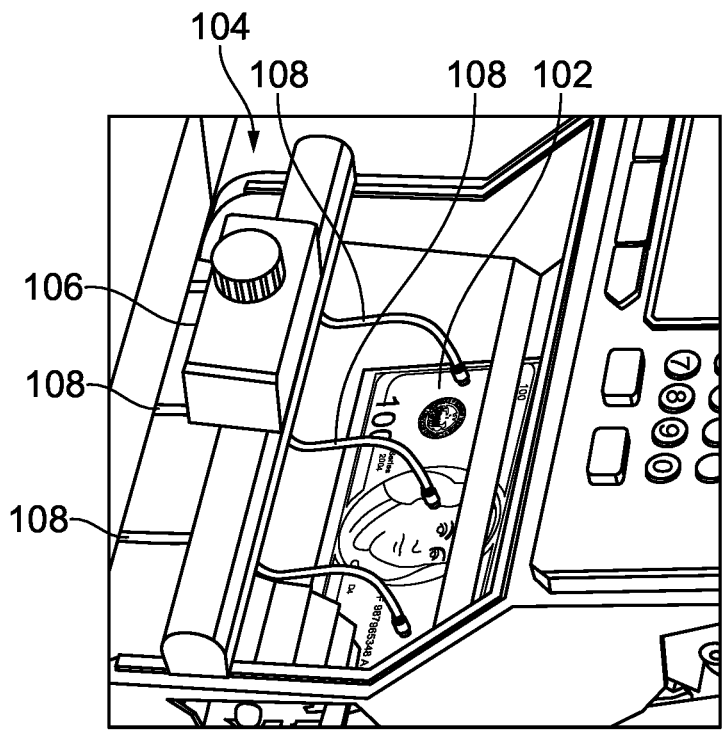
FIG. 2 is an elevated, perspective view of a first embodiment of the currency-counting machine.

Now referring to FIGS. 1 and 2, the sterilizing means according to a first embodiment is a spray mechanism 104 that includes a reservoir 106 with a plurality of dispensing nozzles 108 extending therefrom. The reservoir is filled with a liquid or powder disinfectant and includes a refill cap that can be removed to replenish the disinfectant. The nozzle outlets are positioned to coat both sides of a bank note with disinfectant after counting and during transport to the output tray. The disinfectant is pumped though the nozzles in a conventional fashion using manual pumps, air pumps, electric pumps, or any other similar dispensing mechanism.

Figure 3:
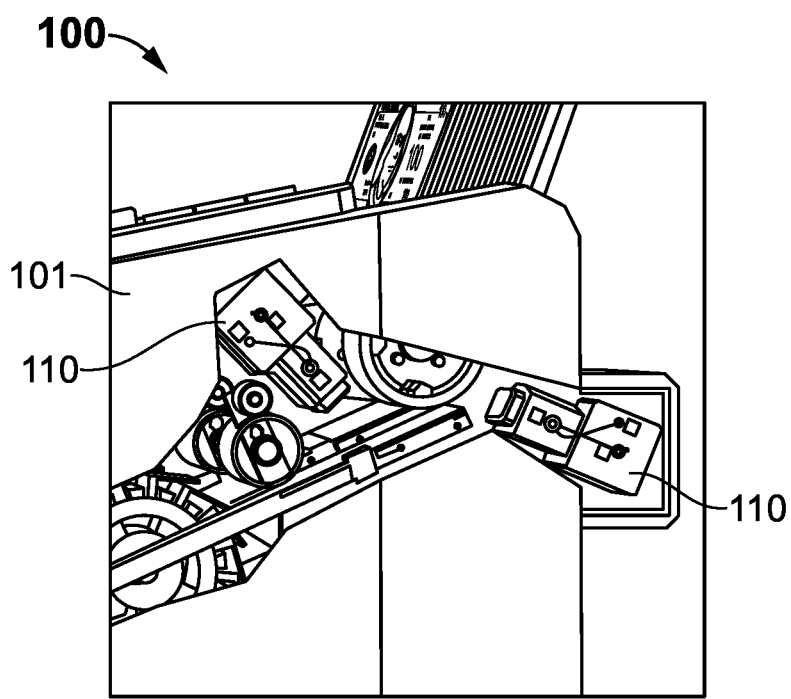
FIG. 3 is a cutaway view of the currency-counting machine.
Figure 4:
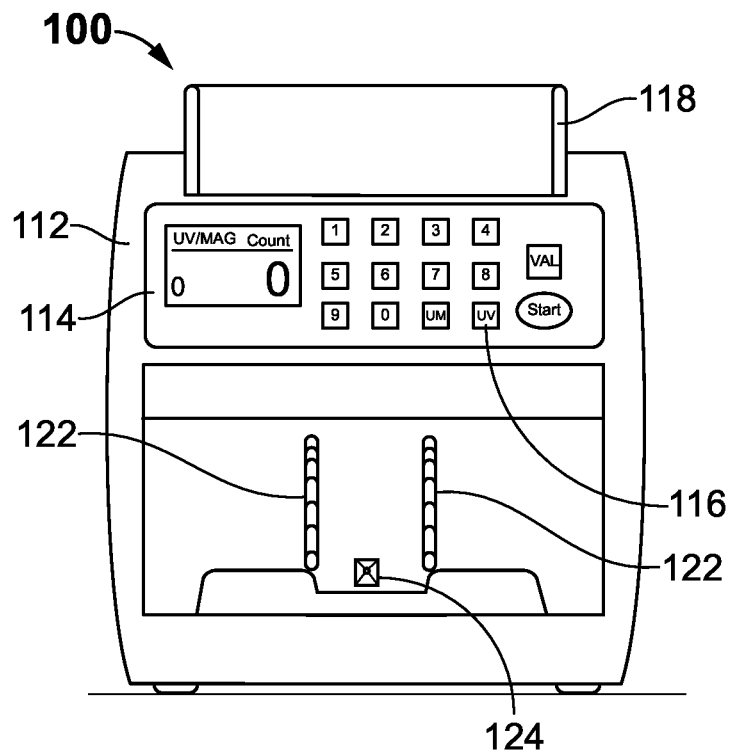
FIG. 4 is a top view of the machine.
Figure 5:
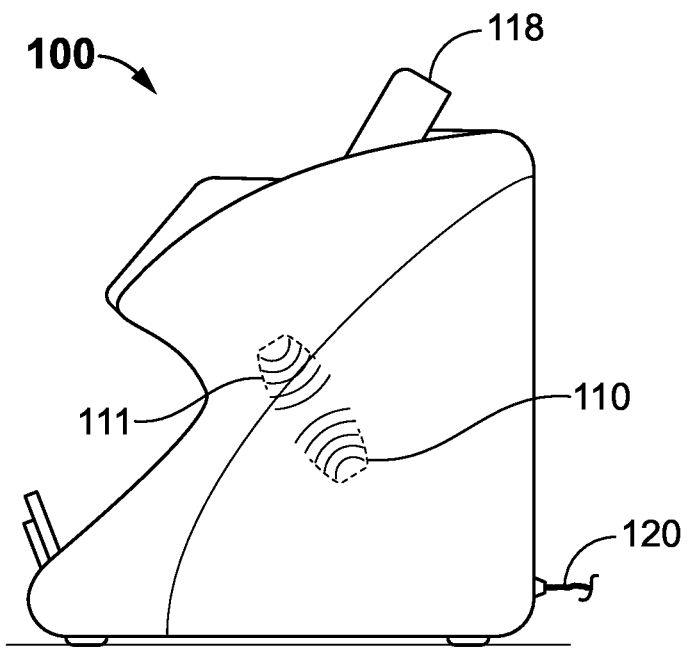
FIG. 5 is a side view of the machine according to another embodiment of the present invention.
Figure 6:
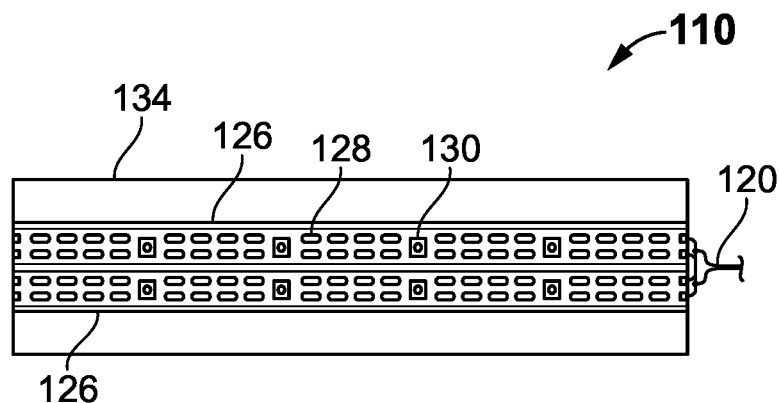
FIG. 6 is a front view of an exemplary UV radiator.
Figure 7:
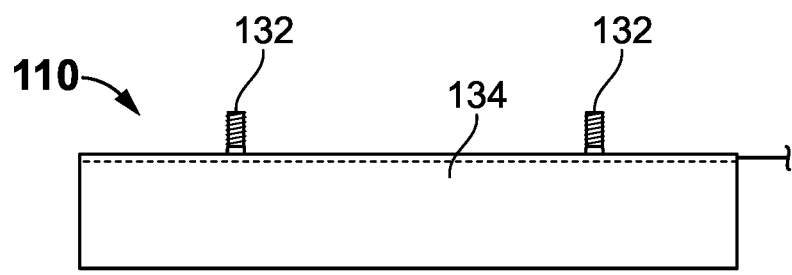
FIG. 7 is a top view of an exemplary UV radiator.
Figure 8:
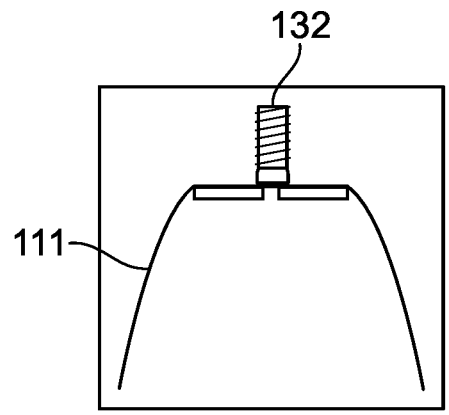
FIG. 8 is an end view of an exemplary UV radiator.
Figure 9:
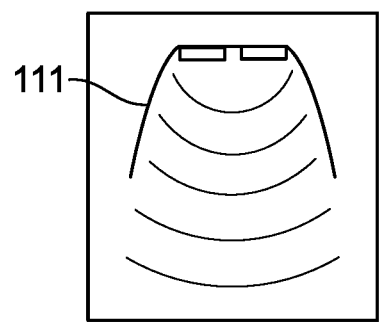
FIG. 9 is an end view of a radiator projecting UV light beams.
Figure 10:
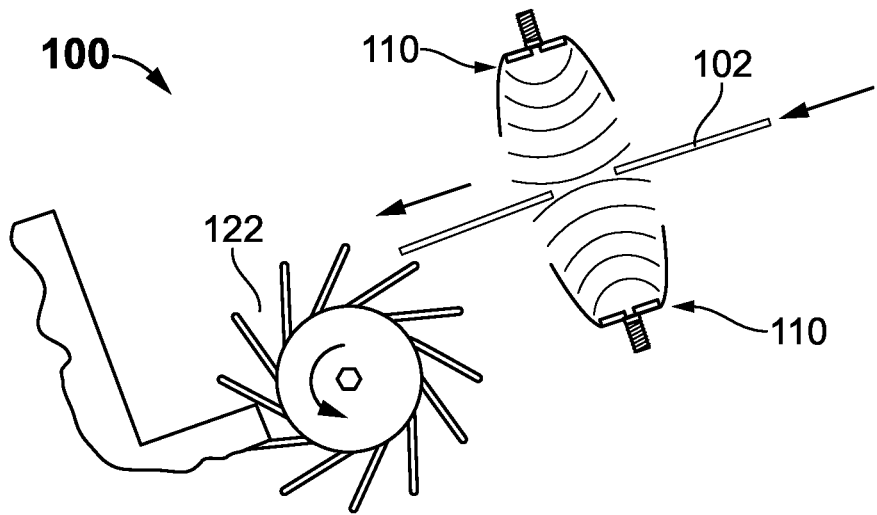
FIG. 10 depicts paper currency being passed beneath a UV radiator.

Now referring to FIG. 3 the sterilizing means according to another embodiment is an ultraviolet light system 110 mounted within a compartment or cavity within the housing interior. The light system 110 includes multiple UVC radiators each including multiple rows of UVC LEDs 128 mounted on a strip 126 for emitting a high-intensity light field to disinfect the notes passing through the housing. The strips 126 are mounted on a substantially C-shaped shield 111 that includes a planar base portion 77 with a pair of spaced sidewalls 134 extending therefrom. The sidewalls capture light emanating from the radiators and funnel it directly onto the notes. A threaded post 132 on the rear surface of the shield allows the light units to be mounted in a desired location in or on the housing. The interior surfaces of the sidewalls 134 are coated with stainless steel to optimize UV light reflection and to provide a heat sink for the LEDs. Each radiator may be positioned within a casing 101 that is oriented to project UV light onto both sides of a bank note. The UV radiators are powered with a cable 120 that is coupled with an electrical receptacle. At least one shield is positioned above and below the currency's path to assure complete exposure to the radiation.

The radiators may also include sensors and software for detecting counterfeit or fake currency. Both the UV radiators and spray mechanism could be positioned at the bank note outlet or any other location that allows both sides of the bank note to be sterilized. The UV radiators 110 project high-intensity light having a wavelength of approximately 265 nm that penetrates the DNA of microbes, viruses, pathogens, and germs, as they pass through the concentrated light field. The UVC light also disrupts the ribonucleic links and kills the cells very rapidly. In one embodiment, the UVC light is very effective at killing unwanted organisms, even when the bills are moving very quickly. In the UVC version, both sides of the bill are exposed to the high-intensity light. The high-intensity light does not affect any other operation of the counting machine 100 and does not draw an excessive amount of power above that used by a conventional counting machine. Also, the UCV system will not degrade bills or banknotes 102 and does not affect the machine's counting mechanism.

Figure 11:
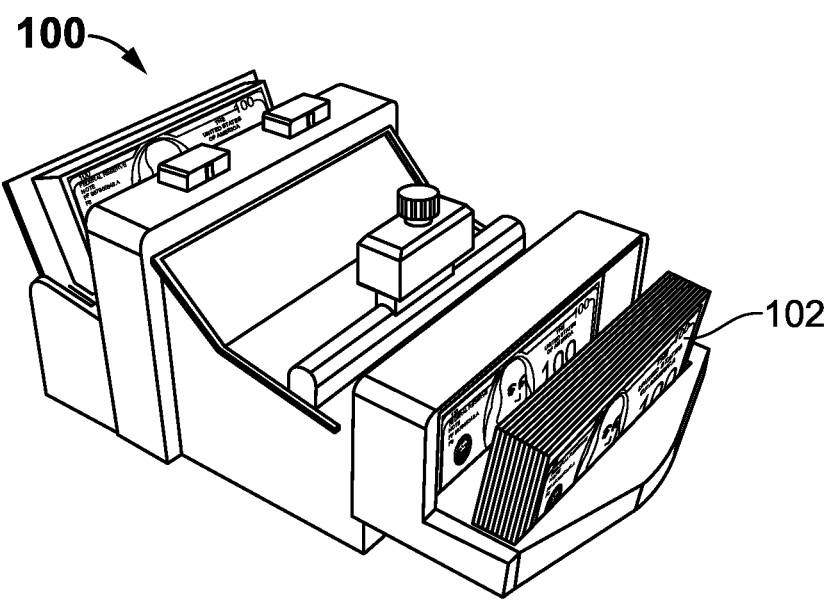
FIG. 11 is a perspective view of the machine without a currency counting mechanism.

Now referring to FIG. 11, the device could be a stand-alone cleaning machine without any internal counting hardware. Bills would be processed and sterilized without totaling the currency but would include a means for feeding bills though the machine as with a conventional money-counting machine.

The above-described device is not limited to the exact details of construction and enumeration of parts provided herein. The sterilizing means could be installed at the bank note outlet or any other location where the entire bank note will be sterilized. Either or both sterilizing mechanisms can be used with or without a counting mechanism. Although the device has been primarily depicted and described as sterilizing paper currency, it can also be used to sterilize coins. Furthermore, the size, shape, and materials of construction of the various components can be varied without departing from the spirit of the present invention.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A machine for sterilizing currency comprising:
   a housing having a front end, a rear end and interior chamber;
   a stacking tray on the front end of the housing;
   a feeding hopper at the rear end of the housing for receiving unsterilized bank notes;
   means for moving currency from said feeding hopper, through said interior chamber and to said stacking tray;
   a reservoir having a disinfectant therein;
   a plurality of dispensing nozzles extending from said reservoir, each of said nozzles having an outlet positioned to coat each of two sides of a bank note as said bank note travels through the interior chamber to said stacking tray.

2. A machine for sterilizing currency comprising:
   a housing having a front end, a rear end and interior chamber;
   a stacking tray on the front end of the housing;
   a feeding hopper at the rear end of the housing for receiving unsterilized bank notes;
   means for moving said bank notes from said feeding hopper, through said interior chamber and to said stacking tray;
   multiple rows of ultraviolet light radiators each including multiple rows of ultraviolet LEDs mounted on a strip for emitting a high-intensity light field to disinfect the bank notes passing through said housing.

3. The machine according to claim 2 wherein said strip is mounted on a substantially C-shaped shield having a planar base portion with a pair of spaced sidewalls extending therefrom that capture ultraviolet light emanating from the ultraviolet light radiators and funnel the ultraviolet light toward said bank notes.

4. The machine according to claim 3 wherein the spaced sidewalls of said shield are coated with stainless steel to optimize ultraviolet light reflection and to provide a heat sink for said LEDs.

5. The machine according to claim 4 wherein each of ultraviolet light radiators is positioned within a casing that is oriented to project UV light onto both sides of the bank note.

6. The machine according to claim 5 wherein said C-shaped shield includes a rear surface with a threaded post thereon for mounting said shield in a desired location on said housing or in said interior chamber.

7. The machine according to claim 6 further comprising a sorting, counting, and stacking mechanism within the interior chamber of said housing.

\* \* \* \* \*